United States Patent [19]

Minn

[11] 4,282,153

[45] Aug. 4, 1981

[54] PROCESS FOR PREPARING ESTERS OF O,O-DIALKYL DITHIOPHOSPHORIC ACID

[75] Inventor: James Minn, Hattiesburg, Miss.

[73] Assignee: Boots Hercules Agrochemicals Co., Wilmington, Del.

[21] Appl. No.: 123,549

[22] Filed: Feb. 22, 1980

[51] Int. Cl.$^3$ .............................................. C07D 319/10
[52] U.S. Cl. .................................. 260/340.6; 424/278
[58] Field of Search ....................................... 260/340.6

[56] References Cited

U.S. PATENT DOCUMENTS

| | | | |
|---|---|---|---|
| 2,725,328 | 11/1955 | Diveley et al. | 260/340.6 |
| 2,815,350 | 12/1957 | Speck | 260/340.6 |
| 2,864,826 | 12/1958 | Diveley | 260/340.6 |

*Primary Examiner*—Ethel G. Love
*Attorney, Agent, or Firm*—Hazel L. Deming

[57] ABSTRACT

Disclosed is a method for improving the yields of insecticidal compositions produced by reacting an O,O-dialkyl dithiophosphoric acid with a chloro-p-dioxane in the presence of a Lewis acid catalyst and a stoichiometric excess of the acid reactant. More specifically, the method concerns the improvement wherein certain bicyclo-heptenes are added to the system resulting from the reaction and reacted with the excess of O,O-dialkyl dithiophosphoric acid present in the system.

9 Claims, No Drawings

PROCESS FOR PREPARING ESTERS OF O,O-DIALKYL DITHIOPHOSPHORIC ACID

This invention relates to a process for the preparation of esters of O,O-dialkyl dithiophosphoric acid and more particularly relates to an improved process for producing high yields of a composition containing the esters of O,O-dialkyl dithiophosphoric acid and a chloro-p-dioxane and the composition produced therefrom.

It is known from U.S. Pat. No. 2,725,328 to Diveley and Lohr that organic dithiophosphoric acid esters having excellent insecticidal properties can be prepared by the substitution reaction of an O,O-dialkyl dithiophosphoric acid with a dichloro-p-dioxane and from U.S. Pat. No. 2,815,350 to Speck that the rate of the reaction can be accelerated by carrying out the reaction in the presence of a catalytic amount of a chloride of zinc, iron or tin. Usually the reaction is conducted in a volatile hydrocarbon solvent which is inert in the reaction using an excess over the theoretical amount of one of the reactants to force the reaction to completion. Generally, from the standpoints of cost and environmental concerns it is more advantageous to employ an excess of the O,O-dialkyl dithiophosphoric acid reactant than the chlorodioxane. However, additional processing is still required to separate and recover unreacted acid in order to satisfy safety and environmental regulations. Thus, any economic advantages in yield which are realizable by the use of excess acid reactant are offset, at least in part, by the costs associated with recovery.

Further, it is known to the art that high yields of the mono-adducts of O,O-dialkyl dithiophosphoric acids and certain olefins or diolefins can be obtained by a free radical initiated addition reaction, and that similar results can be realized with conjugated dienes by a cationic addition mechanism promoted by an acid medium. See, for example, U.S. Pat. Nos. 2,976,308, 3,340,332; and 3,574,795. Additionally, Whetstone and May, in U.S. Pat. No. 2,767,206, teach carrying out an addition type of reaction with an O,O-dialkyl dithiophosphoric acid and a cycloheptadiene such as bicyclo(2,2,1)2,5-heptadiene itself or its halogen or alkyl substituted analogs in the presence of an aliphatic tertiary amine catalyst and a polymerization inhibitor; and Reese and Brahler, in U.S. Pat. No. 3,023,209, teach a similar substitution reaction with bicyclo(2,2,1)heptene or its derivatives and disclose that the catalyst and polymerization inhibitor are not always necessary.

Now in accordance with this invention it has been found that certain bicyclic alkenes can be used advantageously to form desirable adducts with the excess O,O-dialkyl dithiophosphoric acid remaining in the reaction mixture obtained by carrying out the substitution reaction of a chloro-p-dioxane with a stoichiometric excess of an O,O-dialkyl dithiophosphoric acid in the presence of a catalytic amount of zinc chloride, ferrous chloride or stannous chloride and that the addition reaction of the bicyclic alkene with the acid present in the reaction mixture proceeds rapidly under normal reaction conditions without undesirable side reactions or an adverse effect on the yield or purity of the ester products contained therein. Thus, the invention provides increased yields of a useful pesticidal composition based on the chloro-p-dioxane reactant, minimizes the additional processing required to separate and recover unreacted acid and provides safety and ecological advantages not hereto realizable.

Accordingly, the present invention relates to an improved process for reacting an O,O-dialkyl dithiophosphoric acid with a chloro-p-dioxane in the presence of a catalytic amount of zinc chloride, ferrous chloride or stannous chloride and a stoichiometric excess of said acid, wherein the improvement comprises adding to the system resulting from said reaction from 2.5 to 100 mole % based on the O,O-dialkyl dithiophosphoric acid of a bicyclo(2,2,1)heptene of the formula

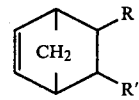

where R and R' are independently hydrogen, alkyl or halogen, or together with the carbon atoms to which they are attached form a condensed hydrocarbon ring containing 5 to 6 carbon atoms, reacting said bicycloheptene with the O,O-dialkyl dithiophosphoric acid present in the system and recovering the resulting product, and the product produced thereby.

The process of this invention is more particularly set forth in the following examples in which all parts and percentages are by weight, unless otherwise indicated.

EXAMPLE 1

A vessel equipped with heating means, agitator, thermometer, addition port and condenser was charged with 490 grams of a 55% cyclohexane solution of O,O-diethyl dithiophosphoric acid (1.45 mole) and 0.7 gram (0.011 gram atom) of zinc dust. Heating and agitation were commenced and when the temperature of the charge reached 80° C., 102 grams (0.65 mole) of 2,3-dichloro-p-dioxane were added gradually over a 1 hour period and a slow current of nitrogen gas was passed through the mixture to carry off the liberated hydrogen chloride. The reaction mixture was agitated at 85° C. for an additional 3 hour period, after which time the mixture was withdrawn from the vessel and cooled to 25° C. A 100 ml. portion of the resulting crude mixture (containing by titrimetric analysis of a separate sample 0.051 mole of unreacted diethyl dithiophosphoric acid) was recharged to the reaction vessel, and 15 grams (0.16 mole) of bicyclo(2,2,1)-heptene-2 were added to the charge over a period of one minute with agitation. An exothermic reaction occurred immediately and after 1 hour the temperature had increased to 29° C. Heating was then commenced and the mixture was agitated at 80° C., for an additional hour, after which time the mixture was cooled to 25° C. The cooled mixture, by titrimetric analysis, contained 0.030 mole of acid, indicating that the amount of excess acid had been reduced by about 41%. The final reaction mixture was washed with 25 ml. of an acidic salt solution (4.9% HCl and 12.8% NaCl) and then with 25 ml. of 25% aqueous sodium hydroxide and the washed solution was heated to remove the cyclohexane by evaporation. The product (53.1 grams) contained 61.6% of the bis(O,O-diethyl dithiophosphate) of p-dioxane-2,3-dithiol, as determined by high pressure liquid chromatography.

EXAMPLE 2

When another 100 ml. portion of the crude mixture of Example 1 was reacted with bicyclo(2,2,1)heptene-2 according to the procedure of Example 1, except that the amount of the heptene-1 reactant was reduced to 5 grams (0.053 mole), titrimetric analysis of the cooled reaction mixture gave a value of 0.043 mole of unreacted acid, indicating that the amount of excess acid had been reduced by 16%. The recovered product was 52.8 grams and contained 62.1% of the bis(O,O-diethyl dithiophosphate) of p-dioxane-2,3-dithiol.

By comparison, direct recovery of the ester product from another 100 ml. portion of the crude reaction mixture (by washing, drying and evaporation in the same manner as Example 1) gave 47.7 grams of a product containing 66.6% of the bis(O,O-diethyl dithiophosphate) of p-dioxane-2,3-dithiol.

EXAMPLE 3

A crude reaction mixture was prepared according to the procedure of Example 1, except that 507 grams of the cyclohexane solution of O,O-diethyl dithiophosphoric acid were used (1.50 mole) and the amount of unreacted acid per 100 ml. of crude was 0.059 mole. A 100 ml. portion of the crude and 16 grams (0.12 mole) of dicyclopentadiene were charged to a reaction vessel, the charge was stirred for 1 hour at room temperature, during which time an exothermic reaction occurred and the temperature increased to 33° C., heating was commenced and the mixture was stirred at 80° C. for an additional hour, following which time the reaction mixture was cooled to 25° C. The cooled mixture, by titrimetric analysis, contained 0.013 mole of unreacted acid, indicating that the amount of excess acid had been reduced by about 78%. Recovery of the product according to the procedure of Example 1 gave 54.7 grams of a product containing 60.7% of bis(O,O-diethyl dithiophosphate) of p-dioxane-2,3-dithiol. By comparison, direct recovery of product from 100 ml. of the crude mixture gave 45.7 grams of a product containing 83.2% of bis(O,O-diethyl dithiophosphate) of p-dioxane-2,3-dithiol.

EXAMPLE 4

When another 100 ml. portion of the crude mixture of Example 3 was reacted with 3.2 grams (0.024 mole) of dicyclopentadiene according to the procedure of Example 3, the final reaction mixture contained 0.036 mole of unreacted acid and 53.4 grams of a product containing 68.6% of bis(O,O-diethyl dithiophosphate) of p-dioxane-2,3-dithiol were obtained.

EXAMPLE 5

When another 100 ml. portion of the crude mixture of Example 3 was reacted with 8 grams (0.060 mole) of dicyclopentadiene according to the procedure of Example 3, the final reaction mixture contained 0.015 mole of unreacted acid and 55.8 grams of a product containing 60.6% of bis(O,O-diethyl dithiophosphate) of p-dioxane-2,3-dithiol were obtained.

As stated, the process of this invention involves carrying out the reaction of an O,O-dialkyl dithiophosphoric acid with a chloro-p-dioxane in the presence of a catalytic amount of a chloride of zinc, iron or tin using stoichiometric excess of the dithiophosphoric acid reactant and then, without isolation of reaction product from the system, adding from 2.5 to 100 mole % based on the dithiophosphoric acid reactant of a specified bicyclo(2,2,1)heptene to the reaction mixture, reacting the bicycloheptene with the O,O-dialkyl dithiophosphoric acid present in the system and recovering the resulting product.

The process of this invention is applicable to any O,O-dialkyl dithiophosphoric acid and is particularly interesting where the alkyl groups are those having 1 to 4 carbon atoms because of the utility of the resulting products as insecticides. However, there is no criticality with respect to the present process insofar as the alkyl groups themselves are concerned and the invention is not limited with respect thereto.

The chloro-p-dioxane reactant used in the process of this invention contains at least one chlorine which is readily replaced by the O,O-dialkyl phosphorodithioate group and preferably is a dichloro-p-dioxane such as 2,3-dichloro-p-dioxane, 2,5-dichloro-p-dioxane, or 2,6-dichloro-p-dioxane, a trichloro-p-dioxane or tetrachloro-p-dioxane.

The first step of the process of this invention is carried out by contacting a stoichiometric excess of the O,O-dialkyl dithiophosphoric acid with the chloro-p-dioxane in the presence of a catalytic amount of a metal chloride catalyst. In theory, one mole of O,O-dialkyl dithiophosphoric acid replaces each reactive chlorine atom present in the chloro-p-dioxane reactant and, in the case of 2,3-dichloro-p-dioxane, stoichiometry requires 2 moles of the dioxane, as shown by the following equation:

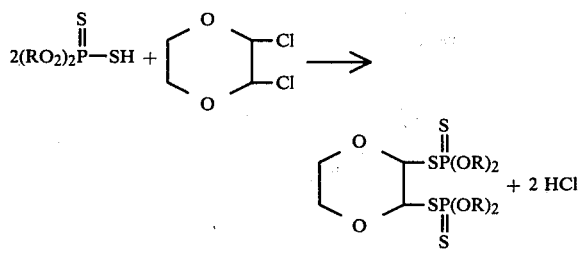

where R is alkyl. Thus, the amount of acid used will depend on the degree of substitution which is to be effected and usually will range from about 5 to about 50%, preferably from about 10 to about 30% in excess of theory. Amounts greater than about 50% in excess of stoichiometry, however, have not been found to provide any additional advantages in yield or product purity and hence are not recommended.

The catalysts which are used in the present process accelerate rather than initiate the reaction and are chlorides of zinc, iron and tin. Zinc and tin chlorides are preferred because they give the lightest colored products. While the catalysts are referred to as chlorides, it is to be understood that metals or salts which under the reaction conditions are converted into the metal chlorides may be used as equivalents because of the nature of the reaction, and it is not intended that the process should be limited to one in which the metal chloride is added as such to the reaction mixture. The amount of catalyst used in the process of the present invention is not critical. A catalytic amount will generally be in the range of about 0.05 to 2 mole percent based on the dithiophosphoric acid reactant, with about 0.5 to about 1.0 mole percent being preferred.

The reaction temperature is any temperature in the range of about 25° to about 110° C. at which reaction takes place but below the decomposition temperature of the product or any intermediate produced in the first step of the process. The particular temperature selected will thus depend upon the reactants used. Since, in general, the rate of the reaction increases as the temperature is elevated, it is usually more efficient to conduct the reaction at temperatures from 75° to 95° C. for 1 to 8 hours and preferably 2 to 5 hours.

The first step of the process is preferably carried out in a solvent which is inert in the reaction, although solvents are not necessary. When a solvent is used, aromatic volatile hydrocarbons such as benzene, toluene, xylenes, chlorobenzene, or cymene, cycloaliphatic volatile hydrocarbon such as cyclopentane or cyclohexane, or carbon tetrachloride are preferred because they have the desired dissolving power for the reaction mixture without high dissolving power for the hydrogen chloride produced and are readily removed after the reaction is complete by distillation. Although water is generally deleterious to substitution reactions of this type, trace amounts of water do not need to be excluded and completely anhydrous catalysts are not necessary.

The second and third steps of the process described by this invention involve adding to the reaction mixture which results from carrying out the first step of the process, from 2.5 to 100 mole %, and preferably from 5 to 50 mole %, based on the O,O-dialkyl dithiophosphoric acid of a bicyclo(2,2,1)heptene of the formula

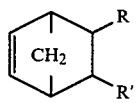

where R and R' are as indicated above, and reacting the heptene with thio acid present in the reaction mixture. Bicyclo(2,2,1)heptenes of the above formula are known compounds and can be derived by the Diels-Alder addition of cyclopentadiene and dienophile compounds. For example, bicyclo(2,2,1)heptene-2 or -5 is the adduct of cyclopentadiene and ethylene. Compounds of the above formula wherein R and R' are halogen such as chlorine or bromine can also be obtained by the reaction of bicyclo(2,2,1)-2,5-heptadiene (derived from cyclopentadiene and acetylene) with the desired halogen. The preferred bicyclo(2,2,1)heptenes are bicyclo(2,2,1)heptene-2 (where R and R' are both hydrogen) and dicyclopentadiene (where R and R' form a cyclic pentene ring).

In most instances, the addition of the bicyclo heptene reactant to the reaction mixture results in an immediate reaction with any O,O-dialkyl dithiophosphoric acid present in the system at room temperature, accompanied by exothermic heat of the reaction. Generally, the reaction takes place within a period of 45 minutes and additional heating is not required. Heating to temperatures of 60° to 90° C. for 1 to 2 hours, however, is not detrimental to product quality and in some cases offers additional advantages in yield.

Following completion of steps two and three, the reaction products produced in the steps of this process are recovered. Isolation is conventional and usually any excess reactants are removed from the organic phase by washing with water or preferably water containing sufficient alkali to produce water-soluble salts and the solvent, if present, is removed by distillation. Purification by selective solvent extraction or by adsorptive agents is not usually necessary and the product does not require subsequent treatments.

The practice of the process of this invention provides directly high yields of a composition containing esters of an O,O-dialkyl dithiophosphoric acid and a chloro-p-dioxane and the adduct of a bicyclo(2,2,1)heptene and O,O-dialkyl dithiophosphoric acid. The compositions, and particularly those containing from 60 to 85% of the bis(O,O-dialkyl dithiophosphates) of p-dioxane dithiol are highly effective insecticides without subsequent treatment and can be used as the sole toxic agent in insecticidal formulations or, if desired, in admixture with other toxicants for modifications of the properties of the individual toxicants.

What I claim and desire to protect by Letters Patent is:

1. In the process for producing a dithiophosphoric acid ester of p-dioxane by reacting an O,O-dialkyl dithiophosphoric acid with a chloro-p-dioxane in the presence of a catalytic amount of zinc chloride, ferrous chloride or stannous chloride and a stoichiometric excess of said acid, the improvement which comprises adding to the system resulting from said reaction from 2.5 to 100 mole % based on the O,O-dialkyl dithiophosphoric acid of a bicyclo(2,2,1)heptene of the formula

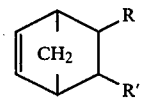

where R and R' are independently hydrogen, alkyl or halogen or together with the carbon atoms to which they are attached form a condensed hydrocarbon ring containing 5 to 6 carbon atoms, reacting said bicycloheptene with the O,O-dialkyl dithiophosphoric acid present in the system whereby an O,O-dialkyl dithiophosphoric acid adduct is formed and recovering the resulting product containing said ester and said adduct.

2. The process of claim 1 wherein the process is carried out in an inert organic solvent.

3. The process of claim 2 in which the solvent is cyclohexane.

4. The process of claim 3 in which the O,O-dialkyl dithiophosphoric acid is O,O-diethyl dithiophosphoric acid.

5. The process of claim 4 in which the chloro-p-dioxane is a dichloro-p-dioxane.

6. The process of claim 5 in which the dichloro-p-dioxane is 2,3-dichloro-p-dioxane.

7. The process of claim 6 in which the amount of bicyclo(2,2,1)heptene is 5 to 50 mole %.

8. The process of claim 7 in which the bicyclo heptene is dicyclopentadiene.

9. The process of claim 7 in which the bicyclo heptene is bicyclo(2,2,1)heptene-2.

* * * * *